US011649352B2

(12) United States Patent
Hamada et al.

(10) Patent No.: US 11,649,352 B2
(45) Date of Patent: May 16, 2023

(54) RESIN COMPOSITION FOR ACOUSTIC MATCHING LAYER, ACOUSTIC MATCHING SHEET, ACOUSTIC WAVE PROBE, ACOUSTIC WAVE MEASURING APPARATUS, METHOD FOR MANUFACTURING ACOUSTIC WAVE PROBE, AND MATERIAL SET FOR ACOUSTIC MATCHING LAYER

(71) Applicant: FUJIFILM Corporation, Tokyo (JP)

(72) Inventors: Kazuhiro Hamada, Kanagawa (JP); Yoshihiro Nakai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 297 days.

(21) Appl. No.: 16/863,258

(22) Filed: Apr. 30, 2020

(65) Prior Publication Data

US 2020/0255652 A1    Aug. 13, 2020

Related U.S. Application Data

(63) Continuation of application No. PCT/JP2018/040438, filed on Oct. 31, 2018.

(30) Foreign Application Priority Data

Nov. 1, 2017   (JP) .............................. JP2017-212211

(51) Int. Cl.
| | | |
|---|---|---|
| *C08L 63/00* | (2006.01) | |
| *C08G 59/50* | (2006.01) | |
| *G01N 29/24* | (2006.01) | |
| *G10K 11/18* | (2006.01) | |
| *G10K 11/36* | (2006.01) | |
| *C08K 5/14* | (2006.01) | |
| *C08K 3/08* | (2006.01) | |

(52) U.S. Cl.
CPC .......... *C08L 63/00* (2013.01); *C08G 59/5033* (2013.01); *G01N 29/2437* (2013.01); *G10K 11/18* (2013.01); *G10K 11/36* (2013.01); *C08K 5/14* (2013.01); *C08K 2003/085* (2013.01); *C08K 2003/0806* (2013.01); *C08K 2003/0856* (2013.01); *C08K 2003/0862* (2013.01); *C08K 2003/0887* (2013.01); *C08K 2003/0893* (2013.01)

(58) Field of Classification Search
CPC . C08L 63/00; C08G 59/5033; G01N 29/2437; G10K 11/18; G10K 11/36; C08K 2003/0806; C08K 2003/0856; C08K 2003/0862; C08K 2003/0887
See application file for complete search history.

(56) References Cited

U.S. PATENT DOCUMENTS

| | | | |
|---|---|---|---|
| 2007/0205697 A1* | 9/2007 | Chaggares | ........... A61B 8/4444 310/311 |
| 2009/0062655 A1 | 3/2009 | Saito | |
| 2011/0021916 A1 | 1/2011 | Morita | |
| 2013/0221805 A1 | 8/2013 | Ogura et al. | |
| 2014/0249419 A1 | 9/2014 | Morita | |
| 2016/0051228 A1* | 2/2016 | Nakai | .................. A61B 8/4444 600/407 |
| 2016/0096294 A1* | 4/2016 | Angelsen | .............. B29C 43/003 264/331.11 |

FOREIGN PATENT DOCUMENTS

| | | |
|---|---|---|
| CN | 101379871 A | 3/2009 |
| CN | 102143423 A | 8/2011 |
| CN | 106543941 A | 3/2017 |
| EP | 2 004 064 A2 | 12/2008 |
| EP | 2 444 166 A1 | 4/2012 |
| JP | 3-295547 A | 12/1991 |
| JP | 8-65436 A | 3/1996 |
| JP | 2000-174991 A | 6/2000 |
| JP | 2004-104629 A | 4/2004 |
| JP | 2006-174991 A | 7/2006 |
| JP | 2009-071393 A | 4/2009 |
| JP | 2009-296055 A | 12/2009 |
| JP | 2015-082764 A | 4/2015 |
| WO | 2009/113432 A1 | 9/2009 |
| WO | 2012/144226 A1 | 10/2012 |

OTHER PUBLICATIONS

Communication dated Jun. 15, 2021, issued by the Japanese Patent Office in corresponding application No. 2019-550438.
Office Action dated May 7, 2021 issued by the Chinese Patent Office in Chinese Application No. English 201880070320.0.
Communication dated Oct. 30, 2020, issued by the State Intellectual Property Office of People's Republic of China in application No. 201880070320.0.
The Extended European Search report dated Nov. 25, 2020, issued by the European Patent Office in application No. 18872229.2.
International Search Report dated Jan. 22, 2019 from the International Searching Authority in International Application No. PCT/JP2018/040438.
Written Opinion dated Jan. 22, 2019 from the International Searching Authority in International Application No. PCT/JP2018/040438.
(Continued)

*Primary Examiner* — Doris L Lee
(74) *Attorney, Agent, or Firm* — Sughrue Mion, PLLC

(57) ABSTRACT

A resin composition for an acoustic matching layer; an acoustic matching sheet formed from the composition; an acoustic wave probe; an acoustic wave measuring apparatus; a method for manufacturing an acoustic wave probe; and a material set, for an acoustic matching layer, that is suitable for preparation of the composition, in which the resin composition for an acoustic matching layer includes a binder including a resin; and metal particles having a monodispersity of 40% to 80%, wherein the monodispersity is calculated by equation (1):

monodispersity (%)=(standard deviation of particle sizes of metal particles/average particle size of metal particles)×100.

15 Claims, 1 Drawing Sheet

(56) References Cited

OTHER PUBLICATIONS

International Preliminary Report on Patentability dated May 5, 2020 from the International Bureau in International Application No. PCT/JP2018/040438.
Extended European Search Report dated Oct. 14, 2022 in corresponding European Application No. 22188712.8.
European Official Communication dated Mar. 14, 2023 in corresponding European Application No. 22 188 712.8.

* cited by examiner

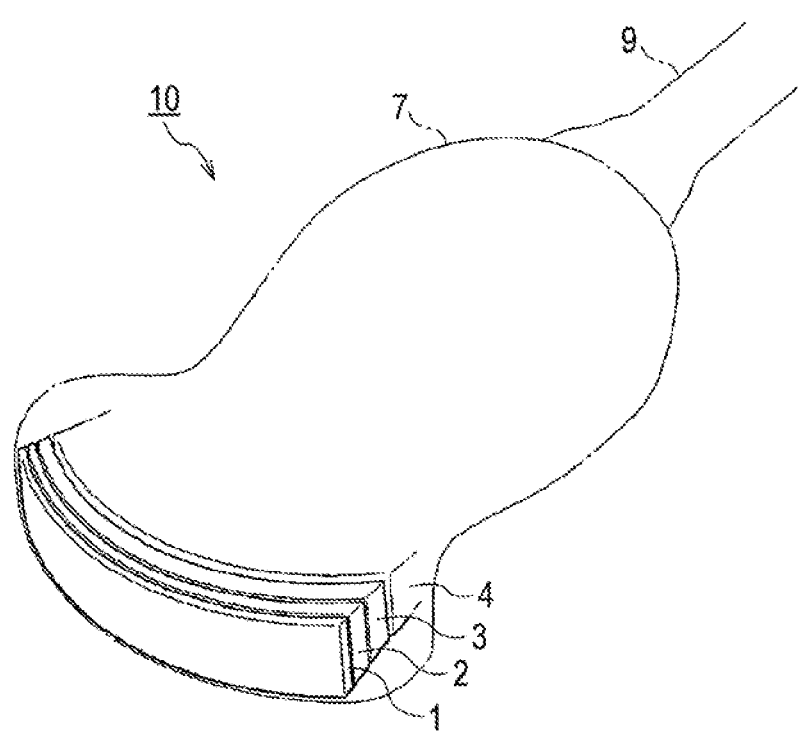

RESIN COMPOSITION FOR ACOUSTIC MATCHING LAYER, ACOUSTIC MATCHING SHEET, ACOUSTIC WAVE PROBE, ACOUSTIC WAVE MEASURING APPARATUS, METHOD FOR MANUFACTURING ACOUSTIC WAVE PROBE, AND MATERIAL SET FOR ACOUSTIC MATCHING LAYER

CROSS-REFERENCE TO RELATED APPLICATIONS

This application is a Continuation of PCT International Application No. PCT/JP2018/040438 filed on Oct. 31, 2018, which claims priority under 35 U.S.C. § 119 (a) to Japanese Patent Application No. 2017-212211 filed in Japan on Nov. 1, 2017. Each of the above applications is hereby expressly incorporated by reference, in its entirety, into the present application.

BACKGROUND OF THE INVENTION

1. Field of the Invention

The present invention relates to resin compositions for acoustic matching layers, acoustic matching sheets, acoustic wave probes, acoustic wave measuring apparatuses, methods for manufacturing acoustic wave probes, and material sets for acoustic matching layers.

2. Description of the Related Art

Acoustic wave measuring apparatuses include an acoustic wave probe configured to irradiate a subject such as a living body with an acoustic wave and to receive the reflected wave (echo) and output a signal. The reflected wave received by the acoustic wave probe is converted into an electrical signal and is displayed as an image. Thus, the acoustic wave probe can be used to visualize and examine the inside of the subject.

Acoustic waves such as ultrasound and photoacoustic waves are selected as appropriate depending on the subject and the measurement conditions.

For example, ultrasound diagnostic apparatuses, which are a type of acoustic wave measuring apparatus, transmit ultrasound toward the inside of the subject, receive the ultrasound reflected by the tissue inside the subject, and display it as an image.

Photoacoustic wave measuring apparatuses, on the other hand, receive an acoustic wave radiated from inside the subject by a photoacoustic effect and display it as an image. The photoacoustic effect is a phenomenon in which, when the subject is irradiated with a pulsed electromagnetic wave such as visible light, near-infrared light, or microwave, the subject absorbs the electromagnetic wave to generate heat that causes the subject to expand thermally, thereby generating an acoustic wave (typically ultrasound).

For acoustic wave measuring apparatuses to transmit and receive an acoustic wave to and from the subject, the acoustic impedance of the acoustic wave probe needs to match that of the subject. To meet this need, the acoustic wave probe is provided with an acoustic matching layer. To explain this, a probe for an ultrasound diagnostic apparatus (also referred to as "ultrasound probe"), which is a type of acoustic wave probe, will be described by way of example.

An ultrasound probe includes a piezoelectric element configured to transmit and receive ultrasound, an acoustic lens for contact with a living body, and an acoustic matching layer disposed between the piezoelectric element and the acoustic lens. The ultrasound transmitted from the piezoelectric element travels through the acoustic matching layer and then through the acoustic lens to enter the living body. There is generally a difference in acoustic impedance (density×sound velocity) between the acoustic lens and the living body. As the difference becomes larger, the ultrasound is more likely to be reflected by the surface of the living body, which decreases the efficiency with which the ultrasound enters the living body. Thus, the acoustic impedance characteristics of the acoustic lens need to be close to those of the living body.

On the other hand, there is generally a large difference in acoustic impedance between the piezoelectric element and the living body. Accordingly, there is also generally a large difference in acoustic impedance between the piezoelectric element and the acoustic lens. Thus, if the piezoelectric element and the acoustic lens are stacked together, the ultrasound generated from the piezoelectric element is reflected at the interface between the piezoelectric element and the acoustic lens, which decreases the efficiency with which the ultrasound enters the living body. To reduce the reflection of the ultrasound at the interface, the acoustic matching layer mentioned above is provided between the piezoelectric element and the acoustic lens. The acoustic impedance of the acoustic matching layer lies between the acoustic impedance of the living body or the acoustic lens and the acoustic impedance of the piezoelectric element so that the ultrasound propagates efficiently from the piezoelectric element into the living body. It is also known to form an acoustic matching layer having a multilayer structure to provide a stepwise gradient in acoustic impedance from the piezoelectric element side toward the acoustic lens side so that the ultrasound propagates more efficiently.

It is known to use a mixture of metal particles and a binder as a material for an acoustic matching layer. By mixing the metal particles to adjust the relative density, the acoustic impedance can be increased to the desired level. By mixing the metal particles, the mechanical strength can also be adjusted. The binder, on the other hand, fills the gaps between the metal particles (i.e., functions as a matrix or dispersion medium). The binder typically includes a resin. The binder also affects the properties, such as acoustic characteristics and mechanical strength, of the acoustic matching layer.

For example, JP2015-82764A discloses that, when acoustic matching test specimens were formed from mixtures of a furan resin, tungsten carbide or titanium oxide particles (heavy particles), and p-toluenesulfonic acid (curing agent), the acoustic impedance of the acoustic matching test specimens was increased to the desired level by adjusting the ratio of the heavy particles to the furan resin.

JP2004-104629A discloses an acoustic matching layer, for an ultrasound probe, that includes a resin and zinc oxide particles. JP2004-104629A reports that the acoustic matching layer having the above configuration can be divided and arranged in an array together with a piezoelectric material.

JP2009-71393A discloses an acoustic matching member including a matrix including an elastomer or resin and a surface-covered composite powder and discloses that the material used for the composite powder is an inorganic material including a transition metal element JP2009-71393A reports that the technique disclosed therein can stably achieve the desired acoustic impedance with good reproducibility.

SUMMARY OF THE INVENTION

In particular, as described above, if an acoustic matching layer has a multilayer structure, the acoustic matching layer needs to be subjected to secondary processing such as cutting or dicing to a thickness level of several hundreds of micrometers or less during the production process. Accordingly, the constituent material for the acoustic matching layer needs to have sufficient formability to resist cracking or other damage during secondary processing. To provide a high-quality acoustic wave probe, the acoustic matching layer also needs to exhibit uniform acoustic characteristics in its entirety. However, the techniques disclosed in the above patent literature do not sufficiently meet these needs.

Accordingly, an object of the present invention is to provide a resin composition, for an acoustic matching layer, that contains metal particles and a binder including a resin, that has good formability, and that can be formed or processed into the desired sheet shape to produce an acoustic matching layer in high yield with little variation in acoustic characteristics in the layer. Another object of the present invention is to provide a material set, for an acoustic matching layer, that is suitable for preparation of such a composition.

Another object of the present invention is to provide an acoustic matching sheet that can be produced in high yield with little variation in acoustic characteristics in the sheet.

Another object of the present invention is to provide an acoustic wave probe that can be manufactured in high yield with little variation in acoustic characteristics in the probe, and also to provide an acoustic wave measuring apparatus including such an acoustic wave probe.

Another object of the present invention is to provide a method for manufacturing an acoustic wave probe by which an acoustic wave probe with little variation in acoustic characteristics in the probe can be manufactured with high efficiency.

After conducting intensive research in view of the foregoing problems, the inventors have found that the use of a mixture of metal particles with a certain variation in particle size and a binder including a resin (also referred to as "matrix" or "dispersion medium") as a composition for forming an acoustic matching layer allows the composition to be formed into a sheet shape and subjected to processing such as grinding into a thin sheet with little likelihood of cracking. The sheet formed from the composition has also been found to have little variation in acoustic characteristics in the sheet.

After conducting further research based on these findings, the inventors have completed the present invention.

Specifically, the foregoing objects of the present invention have been achieved by the following solutions:

[1] A resin composition for an acoustic matching layer includes a binder including a resin; and metal particles having a monodispersity of 40% to 80%, wherein the monodispersity is calculated by equation (1):

$$\text{monodispersity (\%)} = (\text{standard deviation of particle sizes of metal particles/average particle size of metal particles}) \times 100.$$

[2] In the resin composition for an acoustic matching layer according to [1], the metal particles have a monodispersity of 50% to 70%.

[3] In the resin composition for an acoustic matching layer according to [1], the metal particles have a monodispersity of 55% to 65%.

[4] In the resin composition for an acoustic matching layer according to any one of [1] to [3], the metal particles include at least one of Zn, Au, Ag, Zr, Ta, W, Fe, Cu, Ni, Pt, or Mo.

[5] In the resin composition for an acoustic matching layer according to any one of [1] to [4], the metal particles are present in an amount of 60% to 98% by mass.

[6] In the resin composition for an acoustic matching layer according to any one of [1] to [5], the binder includes an epoxy resin and a curing agent.

[7] In the resin composition for an acoustic matching layer according to any one of [1] to [5], the binder includes a rubber and an organic peroxide.

[8] In the resin composition for an acoustic matching layer according to any one of [1] to [5], the binder includes a thermoplastic resin.

[9] An acoustic matching sheet is formed from the resin composition for an acoustic matching layer according to any one of [1] to [8].

[10] An acoustic wave probe has the acoustic matching sheet according to [9] as an acoustic matching layer.

[11] An acoustic wave measuring apparatus includes the acoustic wave probe according to [10].

[12] The acoustic wave measuring apparatus according to [11] is an ultrasound diagnostic apparatus.

[13] A method for manufacturing an acoustic wave probe includes forming an acoustic matching layer on a piezoelectric element using the resin composition for an acoustic matching layer according to any one of [1] to [8].

[14] A material set for an acoustic matching layer includes a base resin made of a resin composition including an epoxy resin and metal particles; and a curing agent for the epoxy resin. The metal particles have a monodispersity of 40% to 80%, wherein the monodispersity is calculated by equation (1):

$$\text{monodispersity (\%)} = (\text{standard deviation of particle sizes of metal particles/average particle size of metal particles}) \times 100.$$

[15] A material set for an acoustic matching layer includes a base resin made of a resin composition including a rubber and metal particles; and a crosslinking agent including an organic peroxide. The metal particles have a monodispersity of 40% to 80%, wherein the monodispersity is calculated by equation (1):

$$\text{monodispersity (\%)} = (\text{standard deviation of particle sizes of metal particles/average particle size of metal particles}) \times 100.$$

The resin composition for an acoustic matching layer and the material sets for an acoustic matching layer according to the present invention exhibit good formability when used to form a desired thin sheet and that can be used to produce an acoustic matching sheet in high yield with little variation in acoustic characteristics in the sheet.

In addition, the acoustic matching sheet according to the present invention can be manufactured in high yield with little variation in acoustic characteristics in the sheet.

In addition, the acoustic wave probe and the acoustic wave measuring apparatus including the acoustic wave probe according to the present invention can be manufactured in high yield with little variation in acoustic characteristics in the probe.

In addition, the method for manufacturing an acoustic wave probe according to the present invention allows an acoustic wave probe with little variation in acoustic characteristics in the probe to be manufactured with high efficiency.

BRIEF DESCRIPTION OF THE DRAWINGS

FIG. 1 is a perspective see-through view illustrating an example convex ultrasound probe as one form of acoustic wave probe.

DESCRIPTION OF THE PREFERRED EMBODIMENTS

Resin Composition for Acoustic Matching Layer

A resin composition for an acoustic matching layer according to the present invention (hereinafter also simply referred to as "the composition according to the present invention") includes a binder including a resin; and metal particles with a certain variation in particle size.

Binder

The binder present in the composition according to the present invention fills the gaps between the metal particles and functions as a dispersion medium for the metal particles.

The resin present in the binder is preferably a rubber, a thermoplastic resin, or a thermosetting resin.

Examples of rubbers include natural rubber and synthetic rubbers. Examples of synthetic rubbers include isoprene rubber, butadiene rubber, styrene-butadiene rubber, chloroprene rubber, acrylonitrile-butadiene rubber, butyl rubber, ethylene-propylene rubber, ethylene-propylene-diene rubber, urethane rubber, silicone rubber, fluorocarbon rubber, chlorosulfonated polyethylene, chlorinated polyethylene, acrylic rubber, polysulfide rubber, and epichlorohydrin rubber. These rubbers may be used alone or in combination.

The thermoplastic resin preferably has a melting point of 100° C. to 350° C. If the composition according to the present invention has a thermoplastic resin as the binder, the thermoplastic resin is solid in a temperature range below the melting point of the thermoplastic resin, and the metal particles are dispersed in the solidified resin.

Preferred examples of thermoplastic resins include polyolefin resins (such as polyethylene and polypropylene), polyvinyl resins (such as polyvinyl chloride), thermoplastic polyimide resins, polyamide resins, polyamide-imide resins, polyester resins (such as polyethylene terephthalate and polybutylene terephthalate), polyacetal resins, polyetheretherketone resins, thermoplastic polyurethane resins, polyphenylene sulfide resins, fluorocarbon resins (such as polytetrafluoroethylene and polyvinylidene fluoride), acrylonitrile-butadiene-styrene copolymers, polystyrene resins, meth(acrylic) resins (such as polyacrylates and polymethacrylates), polycarbonate resins, polyethersulfone resins, and polyetherimide resins.

In particular, it is preferred to use at least one of a polyamide resin, an acrylonitrile-butadiene-styrene copolymer, a meth(acrylic) resin, a polyacetal resin, a polycarbonate resin, a polyethersulfone resin, a polyetherimide resin, or a thermoplastic polyurethane resin.

The thermosetting resin may be any thermosetting resin. Examples of thermosetting resins include epoxy resins, phenolic resins, melamine resins, urea resins, unsaturated polyester resins, alkyd resins, thermosetting polyurethane resins, and thermosetting polyimide resins.

In particular, the thermosetting resin that forms the binder preferably includes an epoxy resin to increase the crosslink density and thereby further improve the mechanical strength of the resulting sheet. In this case, the binder preferably includes an epoxy resin in combination with a curing agent. That is, if the binder includes a thermosetting resin, the binder is preferably a combination of an epoxy resin and a curing agent.

If an epoxy resin is used as the thermosetting resin, the epoxy resin preferably includes at least one of a bisphenol A epoxy resin, a bisphenol F epoxy resin, or a phenol novolac epoxy resin.

The bisphenol A epoxy resin that can be used in the present invention may be any bisphenol A epoxy resin, and a wide range of bisphenol A epoxy resins that are commonly used as base resins for epoxy adhesives can be used. Specific preferred examples of such bisphenol A epoxy resins include bisphenol A diglycidyl ethers (such as jER825, jER828, and jER834 (all trade names) available from Mitsubishi Chemical Corporation) and bisphenol A propoxylate diglycidyl ethers (such as those available from Sigma-Aldrich Company).

The bisphenol F epoxy resin that can be used in the present invention may be any bisphenol F epoxy resin, and a wide range of bisphenol F epoxy resins that are commonly used as base resins for epoxy adhesives can be used. Specific preferred examples of such bisphenol F epoxy resins include bisphenol F diglycidyl ethers (such as the trade name EPICLON 830 available from DIC Corporation) and 4,4'-methylenebis(N,N-diglycidylaniline).

The phenol novolac epoxy resin that can be used in the present invention may be any phenol novolac epoxy resin, and a wide range of phenol novolac epoxy resins that are commonly used as base resins for epoxy adhesives can be used. An example of such a phenol novolac epoxy resin is one available as Product No. 406775 from Sigma-Aldrich Company.

The curing agent may be any compound known for use as a curing agent for epoxy resins. Examples of such compounds include aliphatic amines, aromatic amines, dicyandiamide, dihydrazide compounds, acid anhydrides, and phenolic resins. In particular, it is preferred to use at least one of a primary amine or a secondary amine to increase the crosslink density and thereby further improve the mechanical strength of the resulting sheet.

If the composition according to the present invention includes an epoxy resin and a curing agent as the binder, the curing reaction of the epoxy resin in the composition may proceed over time even under mild conditions. Thus, the properties of the composition may change over time and may therefore be unstable. However, for example, if the composition is stored at a temperature of −10° C. or lower, the curing reaction does not occur or is sufficiently inhibited, and the individual components can be stably maintained in the composition.

If an epoxy resin is used as the binder, a material set for an acoustic matching layer is also preferred that separately includes a resin composition including an epoxy resin and metal particles, serving as a base resin, and a curing agent. When an acoustic matching layer is formed, the base resin and the curing agent are mixed together to prepare the composition according to the present invention before the composition is used to form a layer. Thus, an acoustic matching layer can be formed.

The mass ratio of the epoxy resin forming the binder to the curing agent may be adjusted as appropriate depending on, for example, the type of curing agent used. For example, the ratio of the epoxy resin to the curing agent may be 99/1 to 20/80, preferably 90/10 to 40/60.

If the material set for an acoustic matching layer mentioned above is used to prepare the composition according to the present invention by mixing together the base resin and the curing agent before layer formation, the base resin and the curing agent are preferably mixed together such that the mass ratio of the epoxy resin to the curing agent is 99/1 to 20/80, more preferably such that the mass ratio of the epoxy resin to the curing agent is 90/10 to 40/60.

If the binder present in the composition according to the present invention is a resin other than an epoxy resin, the binder may include an organic peroxide as a crosslinking agent in addition to the resin.

Organic peroxides serve as radical precursors to crosslink the resin by radical reactions. Organic peroxides are compounds having at least a carbon atom and an —O—O— bond and generate radicals when decomposed, for example, thermally. Examples of organic peroxides include ketone peroxides, peroxyketals, hydroperoxides, dialkyl peroxides, acyl peroxides, alkyl peresters, diacyl peroxides, monoperoxycarbonates, and peroxydicarbonates.

The use of an organic peroxide allows the resin to form a crosslinked structure to increase the mechanical strength of the resulting sheet. A composition in which the binder is composed of a combination of a resin and an organic peroxide may undergo a curing reaction over time and may thus exhibit unstable properties. However, for example, if the composition is stored at a temperature of −10° C. or lower, the decomposition of the organic peroxide can be inhibited, and the individual components can be stably maintained in the composition.

A material set for an acoustic matching layer is also preferred that separately includes a resin composition including a resin and metal particles, serving as a base resin, and a crosslinking agent including an organic peroxide. When an acoustic matching layer is formed, the base resin and the crosslinking agent are mixed together to prepare the composition according to the present invention before the composition is used to form a layer. Thus, an acoustic matching layer can be formed.

The resin that forms the binder in combination with the organic peroxide is preferably, for example, an unsaturated polyester resin, a polyolefin resin, or a rubber, more preferably an unsaturated polyester resin or a synthetic rubber. The ratio of the resin forming the binder to the organic peroxide may be adjusted as appropriate depending on the purpose. Typically, the ratio (by mass) of the resin to the organic peroxide is about 100/1 to about 5/1.

Metal Particles

The composition according to the present invention contains metal particles having a particular particle size distribution as described later. By adjusting the amount of metal particles present in the composition, the density of the composition can be adjusted, and accordingly, the acoustic impedance of the resulting acoustic matching layer can be adjusted to the desired level. The metal particles may be surface-treated.

The metal particles may be surface-treated by any technique, and common surface treatment techniques can be used. Examples of such techniques include treatment with oils such as hydrocarbon oils, ester oils, and lanolin; treatment with silicones such as dimethyl polysiloxane, methyl hydrogen polysiloxane, and methyl phenyl polysiloxane; treatment with fluorine compounds such as perfluoroalkyl-containing esters, perfluoroalkylsilanes, perfluoropolyethers, and perfluoroalkyl-containing polymers; treatment with silane coupling agents such as 3-methacryloxypropyltrimethoxysilane and 3-glycidoxypropyltrimethoxysilane; treatment with titanium coupling agents such as isopropyltriisostearoyl titanate and isopropyl tris(dioctylpyrophosphate) titanate; metallic soap treatment; treatment with amino acids such as acylglutamic acids; treatment with lecithins such as hydrogenated egg yolk lecithin; collagen treatment; polyethylene treatment, moisture retention treatment; inorganic compound treatment; mechanochemical treatment; and phosphoric acid compound treatment.

The metal forming the metal particles may be any metal. A metal atom may be used alone or in the form of a metal carbide, nitride, oxide, or boride. The metal may also be alloyed. Examples of alloys include high-tensile-strength steel (Fe—C), chromium-molybdenum steel (Fe—Cr—Mo), manganese-molybdenum steel (Fe—Mn—Mo), stainless steel (Fe—Ni—Cr), Alloy 42, invar (Fe—Ni), permendur (Fe—Co), silicon steel (Fe—Si), red brass, tombac (Cu—Zn), nickel-silver (Cu—Zn—Ni), bronze (Cu—Sn), cupronickel (Cu—Ni), shakudo (Cu—Au), constantan (Cu—Ni), duralumin (Al—Cu), Hastelloy (Ni—Mo—Cr—Fe), Monel (Ni—Cu), Inconel (Ni—Cr—Fe), nichrome (Ni—Cr), ferromanganese (Mn—Fe), and cemented carbide (WC/Co).

The metal atom forming the metal particles preferably includes at least one metal atom in Groups 4 to 12 of the periodic table from the viewpoint of versatility and ease of surface modification.

More preferably, the metal atom includes at least one of Zn, Au, Ag, Zr, Ta, W. Fe, Cu, Ni, Pt, or Mo.

To reduce the viscosity of the acoustic composition and to reduce acoustic attenuation, the metal particles used in the present invention preferably have an average particle size of 0.01 to 100 μm, more preferably 1 to 10 μm. As used herein, the "particle size" of the metal particles in the present invention refers to the primary particle size. Thus, "average particle size" refers to the average primary particle size.

As used herein, "average primary particle size" refers to the volume average particle size. The volume average particle size is determined as follows.

The metal particles are added to methanol to a concentration of 0.5% by mass and are dispersed by sonication for 10 minutes. The particle size distribution of the thus-treated metal particles is measured with a laser diffraction/scattering particle size distribution analyzer (the trade name LA-950V2 available from Horiba, Ltd.), and the volume-based median size thereof is determined as the volume average particle size. The median size corresponds to a cumulative volume of 50% when the particle size distribution is represented as a cumulative distribution.

The metal particles present in the composition according to the present invention have a monodispersity of 40% to 80%. The monodispersity is calculated by equation (I):

$$\text{monodispersity (\%)} = (\text{standard deviation of particle sizes of metal particles}/\text{average particle size of metal particles}) \times 100$$

where the unit of the particle sizes of the metal particles based on which (standard deviation of particle sizes of metal particles) is calculated is the same as the unit of the particle sizes of the metal particles based on which (average particle size of metal particles) is calculated.

Because the metal particles present in the composition have a monodispersity in the range of 40% to 80%, the mechanical strength can be further increased. As a result, the composition can be formed into a sheet shape and subjected to processing such as cutting into a thin sheet to produce an acoustic matching sheet with little likelihood of cracking or other damage. In addition, the variation in acoustic characteristics in the acoustic matching sheet can be effectively reduced. Although the mechanism is not fully understood, these are attributable in part to the metal particles varying to a certain extent in particle size and thus being highly uniformly distributed in the composition, for example, such that small- to medium-sized metal particles moderately enter the gaps between large-sized metal particles, which presumably results in uniform strength and physical properties.

The metal particles present in the composition according to the present invention preferably have a monodispersity of 50% to 70%, more preferably 55% to 65%.

The amounts of metal particles and binder present in the composition according to the present invention are adjusted as appropriate depending on, for example, the target acoustic impedance. For example, if an acoustic matching layer composed of a plurality of layers is formed, the composition used for the acoustic matching layer on the piezoelectric element side may contain a relatively large amount of metal particles, whereas the composition used for the acoustic matching layer on the acoustic lens side may contain a relatively small amount of metal particles. This provides a gradient in acoustic impedance from the piezoelectric element side toward the acoustic lens side so that an acoustic wave propagates more efficiently.

The amount of metal particles present in the composition according to the present invention is adjusted as appropriate as described above, typically 60% to 98% by mass, preferably 65% to 92% by mass, more preferably 65% to 88% by mass, even more preferably 68% to 82% by mass.

The amount of binder present in the composition is typically 2% to 40% by mass, preferably 8% to 35% by mass, more preferably 12% to 35% by mass, particularly preferably 18% to 32% by mass.

The composition according to the present invention may be composed of the binder and the metal particles. The composition according to the present invention may further contain other components as long as they do not interfere with the advantages of the present invention. Examples of components, other than the binder and the metal particles, that may be added as appropriate include curing retarders, solvents, dispersing agents, pigments, dyes, antistatic agents, antioxidants, flame retardants, and thermal conductivity improvers.

The total amount of binder and metal particles present in the composition according to the present invention is preferably 80% by mass or more, more preferably 90% by mass or more.

Preparation of Resin Composition for Acoustic Matching Layer

The resin composition for an acoustic matching layer according to the present invention can be prepared, for example, by mixing together the constituent components for the resin composition for an acoustic matching layer. Mixing may be performed by any technique, for example, using an agitator or mixer. For example, the resin composition for an acoustic matching layer according to the present invention can be prepared by kneading with a mixer such as a kneader, a pressure kneader, a Banbury mixer (continuous kneader), or a two-roll mill.

If a rubber is used as the binder, the composition according to the present invention can be prepared by kneading the rubber and the metal particles with a mixer and optionally further mixing an organic peroxide. If an organic peroxide is mixed, relatively gentle agitation is preferred so as not to generate much heat (so that the composition does not become unstable).

If a thermoplastic resin is used as the binder, the components are kneaded at a temperature higher than or equal to the melting point of the resin. Thus, a resin composition, for an acoustic matching layer, in which the metal particles are dispersed in the binder can be prepared.

Alternatively, if a thermosetting resin is used as the binder, a composition, for an acoustic matching layer, in which the metal particles are dispersed in the binder can be prepared by mixing together the uncured binder and the metal particles and optionally further mixing a curing agent. In this case, relatively gentle agitation is preferred so as not to generate much heat (so that the composition does not become unstable).

For a material set, for an acoustic matching layer, that includes a base resin made of a resin composition including an epoxy resin and metal particles and a curing agent for the epoxy resin, or for a material set, for an acoustic matching layer, that includes a base resin made of a resin composition including a resin other than an epoxy resin (e.g., a synthetic rubber) and metal particles and a crosslinking agent including an organic peroxide, the base resin can be prepared by mixing or kneading together the intended resin and the metal particles.

When an acoustic matching layer is formed, the base resin and the curing agent, or the base resin and the organic peroxide, are mixed together and optionally kneaded to obtain the composition according to the present invention. The composition can be formed and cured, for example, by heating, to form an acoustic matching layer or a precursor sheet thereof.

Acoustic Matching Sheet (Acoustic Matching Layer)

The composition according to the present invention can be formed into a sheet shape and optionally subjected to processing such as cutting or dicing to the desired thickness or shape to obtain an acoustic matching sheet. This acoustic matching sheet is used as an acoustic matching layer for an acoustic wave probe. The structure of an acoustic wave probe including the acoustic matching layer will be described later.

If the composition according to the present invention has a rubber as the binder, the composition can be formed into the desired sheet shape, for example, by extrusion molding. Thus, an acoustic matching sheet or a precursor sheet thereof can be obtained. "Precursor sheet" refers to a sheet to be subjected to, for example, secondary processing such as cutting. If the binder includes a crosslinking agent such as an organic peroxide, the composition can be formed and cured by heating.

If the composition according to the present invention has a thermoplastic resin as the binder, the composition is heated to thermally melt the resin, is formed into the desired sheet shape, and is solidified by cooling. Thus, an acoustic matching sheet or a precursor sheet thereof can be formed.

Alternatively, if the composition according to the present invention has a thermosetting resin as the binder, the composition is formed into the desired sheet shape in a low-temperature range where no curing reaction occurs or in a low-temperature range where the curing rate is low. The sheet is then optionally heated or otherwise treated to form a crosslinked structure, thereby curing the sheet. Thus, an acoustic matching sheet or a precursor sheet thereof is obtained. That is, if a composition having a thermosetting resin as the binder is used, the resulting acoustic matching sheet is a cured product formed from the composition according to the present invention so as to have a three-dimensional network structure.

Acoustic Wave Probe

An acoustic wave probe according to the present invention has the acoustic matching sheet formed from the composition according to the present invention as an acoustic matching layer.

An example configuration of the acoustic wave probe according to the present invention is illustrated in FIG. 1. The acoustic wave probe illustrated in FIG. 1 is an ultrasound probe for an ultrasound diagnostic apparatus. An ultrasound probe is an acoustic wave probe that uses, particularly, ultrasound as an acoustic wave. Thus, the basic structure of an ultrasound probe can be directly applied to an acoustic wave probe.

Ultrasound Probe

An ultrasound probe 10 is one of the main components of an ultrasound diagnostic apparatus and has the functions of generating ultrasound and transmitting and receiving an ultrasound beam. As shown in FIG. 1, the configuration of the ultrasound probe 10 includes, in order from the distal side (the side to be brought into contact with a living body serving as a subject), an acoustic lens 1, an acoustic matching layer 2, a piezoelectric element layer 3, and a backing material 4. Recently, there has also been proposed an ultrasound probe including a stack of an ultrasonic vibrator (piezoelectric element) for transmission and an ultrasonic vibrator (piezoelectric element) for reception that are formed of different materials in order to receive higher-order harmonics.

Piezoelectric Element Layer

The piezoelectric element layer 3 is a portion that generates ultrasound and has electrodes attached to both sides of the piezoelectric element. As a voltage is applied to the piezoelectric element, it vibrates by repeatedly shrinking and expanding, thus generating ultrasound.

As materials for piezoelectric elements, so-called ceramic inorganic piezoelectric materials have been widely used, including single crystals such as those of quartz, $LiNbO_3$, $LiTaO_3$, and $KNbO_3$, thin films such as those of ZnO and AlN, and sintered bodies such as those of $Pb(Zr,Ti)O_3$-based materials that have been subjected to polarization treatment. In general, piezoelectric ceramics such as lead zirconate titanate (PZT) have been used because of their high conversion efficiency.

Piezoelectric elements for detecting received waves on the high-frequency side also need to be sensitive over a wider bandwidth. Accordingly, organic piezoelectric materials using organic polymer materials such as polyvinylidene fluoride (PVDF) have been used for piezoelectric elements suitable for high-frequency, wide-bandwidth applications.

Furthermore, for example, JP2011-071842A discloses a capacitive micromachined ultrasonic transducer (cMUT) based on micro-electro-mechanical system (MEMS) technology, which provides an array structure with good short-pulse characteristics and wide-bandwidth characteristics, high suitability for mass production, and little characteristic variation.

Any of these piezoelectric element materials is preferred for use in the present invention.

Backing Material

The backing material 4 is disposed on the backside of the piezoelectric element layer 3 and suppresses undesirable vibrations to shorten the width of ultrasound pulses, thereby contributing to an improvement in the distance resolution of an ultrasound diagnostic image.

Acoustic Matching Layer

The acoustic matching layer 2 is provided to reduce the difference in acoustic impedance between the piezoelectric element layer 3 and the subject for efficient transmission and reception of ultrasound.

Acoustic Lens

The acoustic lens 1 is provided to focus ultrasound in the slice direction by refraction to improve the resolution. It is desirable that the acoustic lens 1 come into close contact with a living body serving as a subject and allow ultrasound to match the acoustic impedance of the living body (for the human body, 1.4 to $1.7 \times 10^6$ $kg/m^2/sec$). It is also desirable that the acoustic lens 1 itself exhibit little ultrasound attenuation.

That is, the use of a material in which the sound velocity is sufficiently lower than in the human body, which exhibits little ultrasound attenuation, and whose acoustic impedance is close to that of the human skin as the material for the acoustic lens 1 increases the transmission and reception sensitivity for ultrasound.

The operation of the thus-configured ultrasound probe 10 will be described. As a voltage is applied between the electrodes disposed on both sides of the piezoelectric element, the piezoelectric element layer 3 resonates to transmit an ultrasound signal from the acoustic lens 1 to the subject. Upon reception, the piezoelectric element layer 3 vibrates in response to the signal reflected from the subject (echo signal). This vibration is converted into an electrical signal to obtain an image.

Manufacture of Acoustic Wave Probe

The acoustic wave probe according to the present invention can be produced in a usual manner except that the resin composition for an acoustic matching layer according to the present invention is used. Specifically, a method for manufacturing the acoustic wave probe according to the present invention includes forming an acoustic matching layer on a piezoelectric element using the resin composition for an acoustic matching layer according to the present invention.

Typically, an acoustic lens is further formed on the acoustic matching layer using a material for forming the acoustic lens.

Acoustic Wave Measuring Apparatus

An acoustic wave measuring apparatus according to the present invention has the acoustic wave probe according to the present invention. The acoustic wave measuring apparatus has the functions of indicating the signal intensity of a signal received by the acoustic wave probe and converting the signal into an image.

It is also preferred that the acoustic wave measuring apparatus according to the present invention be an ultrasound measuring apparatus including an ultrasound probe.

EXAMPLES

The present invention will hereinafter be described in more detail with reference to examples in which ultrasound was used as an acoustic wave. The present invention, however, is not limited to ultrasound, but may also be applied to acoustic waves at audible frequencies as long as an appropriate frequency is selected depending on, for example, the subject and the measurement conditions.

Adjustment of Monodispersity of Metal Particles

Metal particles were classified with an electromagnetic sieve shaker (the trade name PRO available from Fritsch) for each type of metal particle. The classified particles were mixed in combination depending on the target monodispersity to obtain metal particles differing in monodispersity. The standard deviation of the particle sizes and the average particle size of the metal particles were determined with a laser diffraction/scattering analyzer (the trade name LA-960 available from Horiba, Ltd.).

The metal particles (before classification) used in the examples are shown below:

Iron particles (Fe, the trade name EW-I available from BASF, average particle size: 2 μm)

Zinc particles (Zn, pulverized by ourselves, average particle size: 4 μm)

Gold particles (Au, pulverized by ourselves, average particle size: 2 μm)
Silver particles (Ag, pulverized by ourselves, average particle size: 2 μm)
Zirconium particles (Zr, pulverized by ourselves, average particle size: 3 μm)
Tantalum particles (Ta, pulverized by ourselves, average particle size: 3 μm)
Copper particles (Cu, pulverized by ourselves, average particle size: 4 μm)
Nickel particles (Ni, pulverized by ourselves, average particle size: 3 μm)
Platinum particles (Pt, pulverized by ourselves, average particle size: 2 μm)
Titanium particles (Ti, pulverized by ourselves, average particle size: 3 μm)
Aluminum particles (Al, pulverized by ourselves, average particle size: 3 μm)

Preparation Example 1: Preparation of Resin Compositions for Acoustic Matching Layers (Binder: Rubber in Combination with Organic Peroxide)

The metal particles and rubbers ((A-1) to (A-9)) were mixed together in the amounts shown in the following tables, and the mixtures were kneaded with a twin-screw mixer (the trade name Labo Plastomill Model C available from Toyo Seiki Seisaku-sho, Ltd.) at 40° C. and a screw rotational speed of 15 rpm for 20 minutes. Thereafter, an organic peroxide (the trade name PERCUMYL D-40 available from NOF Corporation) was added as a crosslinking agent, and the mixtures were further kneaded at 40° C. and 15 rpm for 20 minutes.

Thus, resin compositions, for acoustic matching layers, in which the binder was composed of a combination of a rubber and an organic peroxide were prepared.

Preparation Example 2: Preparation of Resin Compositions for Acoustic Matching Layers (Binder: Thermoplastic Resin)

The metal particles and thermoplastic resins ((A-13) to (A-24)) were mixed together in the amounts shown in the following tables, and the mixtures were kneaded with a twin-screw mixer (the trade name Labo Plastomill Model C available from Toyo Seiki Seisaku-sho, Ltd.). The kneading conditions were as follows: the temperature was 20° C. above the melting point of the thermoplastic resin, the screw rotational speed was 15 rpm, and the kneading time was 20 minutes.

Thus, resin compositions, for acoustic matching layers, that had a thermoplastic resin as the binder were prepared.

Preparation Example 3: Preparation of Resin Compositions for Acoustic Matching Layers (Binder: Epoxy Resin in Combination with Curing Agent)

The metal particles and epoxy resins ((A-10) to (A-12)) were mixed together in the amounts shown in the following tables, and m-phenylenediamine was further mixed as a curing agent. Specifically, the metal particles and the epoxy resins were degassed at room temperature under a reduced pressure of 1.0 Pa with agitation at 1,800 rpm in an agitator (the trade name Awatori Rentaro ARV-310 available from Thinky Corporation) for 4 minutes. To the mixtures was added m-phenylenediamine, followed by further degassing with agitation under the same conditions.

Thus, resin compositions, for acoustic matching layers, in which the binder was composed of a combination of an epoxy resin and a curing agent were prepared.

Test Example 1: Density (Relative Density)

Each of the compositions obtained in Preparation Examples 1 to 3 was used to form a sheet with a length of 60 mm, a width of 60 mm, and a thickness of 2 mm.

If the binder was composed of a combination of a rubber and an organic peroxide, the composition (compound) was placed into a mold and was subjected to hot pressing (at 60° C. to 150° C.) to form the sheet (cured product).

If the binder was a thermoplastic resin, the composition was compression-molded at a temperature of 10° C. above the melting point of the thermoplastic resin and was then trimmed to form the sheet.

If the binder was composed of a combination of an epoxy resin and a curing agent, the composition was cast into a sheet shape and was allowed to stand at a temperature of 80° C. for 18 hours and then at a temperature of 150° C. for 1 hour to form the sheet (cured product).

The density of the resulting sheet at 25° C. was measured in accordance with the method of density measurement specified as Method A (immersion method) in JIS K 7112 (1999) with an electronic densimeter (the trade name "SD-200L" available from Alfa Mirage Co., Ltd.).

The results are shown in the following tables.

Test Example 2: Formability

Sheets having a length of 50 mm, a width of 50 mm, and a thickness of 0.4 mm were formed as in Test Example 1 above. The resulting sheets were polished to a thickness of 200 μm by wet polishing.

Ten sheets were formed from the same composition and were similarly polished. The polished thin sheets were examined under a light microscope. The number of cracked sheets among the ten sheets was counted and rated on the following rating scale to evaluate the formability of the composition.
Rating Scale of Formability
A: All ten sheets were not cracked.
B: One of the ten sheets was cracked.
C: Two of the ten sheets were cracked.
D: Three or more of the ten sheets were cracked.
The results are shown in the following tables.

Test Example 3: Variation in Acoustic Impedance (AI)

Sheets having a length of 5 cm, a width of 5 cm, and a thickness of 2 mm were formed as in Test Example 1 above. The acoustic impedance of each sheet was calculated as the product of the density (in $g/cm^3$) and the sound velocity (in m/sec) (i.e., density×sound velocity) at a total of five positions, i.e., near the four corners and in the center of the sheet. The standard deviation of the acoustic impedances at the five positions was determined and rated on the following rating scale to evaluate the variation in acoustic characteristics.
Sound Velocity
The ultrasound velocity (in m/sec) was measured in accordance with JIS Z 2353 (2003) at 25° C. with a sing-around sound velocity measuring apparatus (the trade name "Type UVM-2" available from Ultrasonic Engineering Co., Ltd.). The ultrasound velocity was measured over the entire area inside a circle with a diameter of 1.5 cm (i.e., the size of a single-channel small probe) at each of the five measurement positions.

Density

The density at 25° C. was measured at the five measurement positions in accordance with the method of density measurement specified as Method A (immersion method) in JIS K 7112 (1999) with an electronic densimeter (the trade name "SD-200L" available from Alfa Mirage Co., Ltd.). Here, the density at each measurement position was determined by cutting a 10 mm×10 mm square piece of sheet from the sound velocity measurement area (a circle with a diameter of 1.5 cm) and measuring the density (in g/cm$^3$) of the cut piece of sheet (10 mm×10 mm square).

Rating Scale of Variation in Acoustic Characteristics
A: standard deviation of less than 0.5
B: standard deviation of from 0.5 to less than 0.7
C: standard deviation of from 0.7 to less than 0.9
D: standard deviation of 0.9 or more The results are shown in the following tables.

TABLE 1-1

| | | Binder | | | Metal particles | | | | |
|---|---|---|---|---|---|---|---|---|---|
| | Resin | Amount of m-phenylene-diamine used*[1] | Amount of organic peroxide used*[1] | Amount present in composition*[2] (% by mass) | Type | Mono-dispersity (%) | Amount present in composition (% by mass) | Density (g/cm$^3$) | Formability | Variation in AI |
| Example 1 | (A-1) | — | 2 | 25 | Fe | 42 | 75 | 3.3 | B | B |
| Example 2 | (A-1) | — | 2 | 25 | Fe | 47 | 75 | 3.3 | B | B |
| Example 3 | (A-1) | — | 2 | 25 | Fe | 54 | 75 | 3.3 | A | B |
| Example 4 | (A-1) | — | 2 | 25 | Fe | 56 | 75 | 3.3 | A | A |
| Example 5 | (A-1) | — | 2 | 25 | Fe | 63 | 75 | 3.3 | A | A |
| Example 6 | (A-1) | — | 2 | 25 | Fe | 68 | 75 | 3.3 | A | B |
| Example 7 | (A-1) | — | 2 | 25 | Fe | 74 | 75 | 3.3 | B | B |
| Example 8 | (A-1) | — | 2 | 25 | Fe | 79 | 75 | 3.3 | B | B |
| Example 9 | (A-2) | — | 2 | 25 | Fe | 56 | 75 | 3.3 | A | A |
| Example 10 | (A-3) | — | 2 | 25 | Fe | 56 | 75 | 3.3 | A | A |
| Example 11 | (A-4) | — | 2 | 25 | Fe | 56 | 75 | 3.3 | A | A |
| Example 12 | (A-5) | — | 2 | 25 | Fe | 56 | 75 | 3.3 | B | A |
| Example 13 | (A-6) | — | 2 | 25 | Fe | 56 | 75 | 3.3 | B | A |
| Example 14 | (A-7) | — | 2 | 25 | Fe | 56 | 75 | 3.3 | A | A |
| Example 15 | (A-8) | — | 2 | 25 | Fe | 56 | 75 | 3.3 | A | A |
| Example 16 | (A-9) | — | 2 | 25 | Fe | 56 | 75 | 3.3 | B | A |
| Example 17 | (A-10) | 10 | — | 25 | Fe | 42 | 75 | 3.3 | B | B |
| Example 18 | (A-10) | 10 | — | 25 | Fe | 47 | 75 | 3.3 | B | B |
| Example 19 | (A-10) | 10 | — | 25 | Fe | 54 | 75 | 3.3 | A | B |
| Example 20 | (A-10) | 10 | — | 25 | Fe | 56 | 75 | 3.3 | A | A |
| Example 21 | (A-10) | 10 | — | 25 | Fe | 63 | 75 | 3.3 | A | A |
| Example 22 | (A-10) | 10 | — | 25 | Fe | 68 | 75 | 3.3 | A | B |
| Example 23 | (A-10) | 10 | — | 25 | Fe | 74 | 75 | 3.3 | B | B |
| Example 24 | (A-10) | 10 | — | 25 | Fe | 79 | 75 | 3.3 | B | B |
| Example 25 | (A-11) | 10 | — | 25 | Fe | 56 | 75 | 3.3 | A | A |
| Example 26 | (A-12) | 10 | — | 25 | Fe | 56 | 75 | 3.3 | B | A |
| Example 27 | (A-13) | — | — | 25 | Fe | 56 | 75 | 3.3 | B | A |
| Example 28 | (A-14) | — | — | 25 | Fe | 56 | 75 | 3.3 | A | A |
| Example 29 | (A-15) | — | — | 25 | Fe | 56 | 75 | 3.3 | A | A |
| Example 30 | (A-16) | — | — | 25 | Fe | 56 | 75 | 3.3 | B | A |

*[1]parts by mass based on 100 parts by mass of resin
*[2]amount of binder present in composition

TABLE 1-2

| | | Binder | | | Metal particles | | | | |
|---|---|---|---|---|---|---|---|---|---|
| | Resin | Amount of m-phenylene-diamine used*[1] | Amount of organic peroxide used*[1] | Amount present in composition*[2] (% by mass) | Type | Mono-dispersity (%) | Amount present in composition (% by mass) | Density (g/cm$^3$) | Formability | Variation in AI |
| Example 31 | (A-17) | — | — | 25 | Fe | 56 | 75 | 3.3 | B | A |
| Example 32 | (A-18) | — | — | 25 | Fe | 56 | 75 | 3.3 | B | A |
| Example 33 | (A-19) | — | — | 25 | Fe | 56 | 75 | 3.3 | B | A |
| Example 34 | (A-20) | — | — | 25 | Fe | 56 | 75 | 3.3 | A | A |
| Example 35 | (A-21) | — | — | 25 | Fe | 56 | 75 | 3.3 | A | A |
| Example 36 | (A-22) | — | — | 25 | Fe | 56 | 75 | 3.3 | B | A |
| Example 37 | (A-23) | — | — | 25 | Fe | 56 | 75 | 3.3 | B | A |
| Example 38 | (A-24) | — | — | 25 | Fe | 56 | 75 | 3.3 | B | A |
| Example 39 | (A-10) | 10 | — | 25 | Zn | 56 | 75 | 3.3 | A | A |
| Example 40 | (A-10) | 10 | — | 30 | Au | 56 | 70 | 3.6 | A | A |
| Example 41 | (A-10) | 10 | — | 27 | Ag | 56 | 73 | 3.5 | A | A |
| Example 42 | (A-10) | 10 | — | 25 | Zr | 56 | 75 | 3.2 | A | A |
| Example 43 | (A-10) | 10 | — | 26 | Ta | 56 | 74 | 3.6 | A | A |

TABLE 1-2-continued

|  | | Binder | | | Metal particles | | | | |
| --- | --- | --- | --- | --- | --- | --- | --- | --- | --- |
|  | Resin | Amount of m-phenylene-diamine used*1 | Amount of organic peroxide used*1 | Amount present in composition*2 (% by mass) | Type | Mono-dispersity (%) | Amount present in composition (% by mass) | Density (g/cm³) | Formability | Variation in AI |
| Example 44 | (A-10) | 10 | — | 25 | Cu | 56 | 75 | 3.3 | A | A |
| Example 45 | (A-10) | 10 | — | 25 | Ni | 56 | 75 | 3.3 | A | A |
| Example 46 | (A-10) | 10 | — | 30 | Pt | 56 | 70 | 3.6 | A | A |
| Example 47 | (A-10) | 10 | — | 20 | Ti | 56 | 80 | 3.5 | A | B |
| Example 48 | (A-10) | 10 | — | 25 | Al | 56 | 75 | 3.5 | A | B |
| Example 49 | (A-1) | — | 2 | 40 | Fe | 56 | 60 | 2.4 | B | A |
| Example 50 | (A-1) | — | 2 | 15 | Fe | 56 | 85 | 4.3 | A | A |
| Example 51 | (A-1) | — | 2 | 2 | Fe | 56 | 98 | 7.1 | A | A |
| Example 52 | (A-10) | 10 | — | 40 | Fe | 56 | 60 | 2.4 | A | A |
| Example 53 | (A-10) | 10 | — | 15 | Fe | 56 | 85 | 4.3 | A | A |
| Example 54 | (A-10) | 10 | — | 2 | Fe | 56 | 98 | 7.1 | A | A |
| Example 55 | (A-14) | — | — | 40 | Fe | 56 | 60 | 2.4 | B | A |
| Example 56 | (A-14) | — | — | 15 | Fe | 56 | 85 | 4.3 | A | A |
| Example 57 | (A-14) | — | — | 2 | Fe | 56 | 98 | 7.1 | A | B |
| Example 58 | (A-10) | 10 | — | 50 | Fe | 56 | 50 | 5.2 | A | B |
| Example 59 | (A-10) | 10 | — | 75 | Fe | 56 | 25 | 1.5 | B | B |
| Example 60 | (A-10) | 10 | — | 50 | Ti | 56 | 50 | 1.9 | B | B |
| Example 61 | (A-10) | 10 | — | 50 | Al | 56 | 50 | 1.7 | B | B |

*1 parts by mass based on 100 parts by mass of resin
*2 amount of binder present in composition

TABLE 1-3

|  | | Binder | | | Metal particles | | | | |
| --- | --- | --- | --- | --- | --- | --- | --- | --- | --- |
|  | Resin | Amount of m-phenylene-diamine used*1 | Amount of organic peroxide used*1 | Amount present in composition*2 (% by mass) | Type | Mono-dispersity (%) | Amount present in composition (% by mass) | Density (g/cm³) | Formability | Variation in AI |
| Comparative Example 1 | (A-1) | — | 2 | 25 | Fe | 32 | 75 | 3.3 | C | C |
| Comparative Example 2 | (A-1) | — | 2 | 25 | Fe | 38 | 75 | 3.3 | B | C |
| Comparative Example 3 | (A-1) | — | 2 | 25 | Fe | 82 | 75 | 3.3 | D | C |
| Comparative Example 4 | (A-1) | — | 2 | 25 | Fe | 90 | 75 | 3.3 | D | D |
| Comparative Example 5 | (A-4) | — | 2 | 25 | Fe | 38 | 75 | 3.3 | C | C |
| Comparative Example 6 | (A-4) | — | 2 | 25 | Fe | 82 | 75 | 3.3 | D | C |
| Comparative Example 7 | (A-5) | — | 2 | 25 | Fe | 38 | 75 | 3.3 | C | C |
| Comparative Example 8 | (A-5) | — | 2 | 25 | Fe | 82 | 75 | 3.3 | D | C |
| Comparative Example 9 | (A-10) | 10 | — | 25 | Fe | 32 | 75 | 3.3 | C | C |
| Comparative Example 10 | (A-10) | 10 | — | 25 | Fe | 38 | 75 | 3.3 | B | C |
| Comparative Example 11 | (A-10) | 10 | — | 25 | Fe | 82 | 75 | 3.3 | C | C |
| Comparative Example 12 | (A-10) | 10 | — | 25 | Fe | 90 | 75 | 3.3 | D | D |
| Comparative Example 13 | (A-14) | — | — | 25 | Fe | 38 | 75 | 3.3 | B | C |
| Comparative Example 14 | (A-14) | — | — | 25 | Fe | 82 | 75 | 3.3 | C | C |
| Comparative Example 15 | (A-10) | 10 | — | 25 | Zn | 38 | 75 | 3.3 | B | C |
| Comparative Example 16 | (A-10) | 10 | — | 25 | Zn | 82 | 75 | 3.3 | C | C |
| Comparative Example 17 | (A-10) | 10 | — | 30 | Au | 38 | 70 | 3.6 | B | C |
| Comparative Example 18 | (A-10) | 10 | — | 30 | Au | 82 | 70 | 3.6 | C | C |
| Comparative Example 19 | (A-10) | 10 | — | 27 | Ag | 38 | 73 | 3.5 | B | C |
| Comparative Example 20 | (A-10) | 10 | — | 27 | Ag | 82 | 73 | 3.5 | C | C |

TABLE 1-3-continued

|  | | Binder | | | Metal particles | | | | |
| --- | --- | --- | --- | --- | --- | --- | --- | --- | --- |
|  | Resin | Amount of m-phenylene-diamine used[*1] | Amount of organic peroxide used[*1] | Amount present in composition[*2] (% by mass) | Type | Mono-dispersity (%) | Amount present in composition (% by mass) | Density (g/cm$^3$) | Formability | Variation in AI |
| Comparative Example 21 | (A-10) | 10 | — | 25 | Zr | 38 | 75 | 3.2 | B | C |
| Comparative Example 22 | (A-10) | 10 | — | 25 | Zr | 82 | 75 | 3.2 | C | C |
| Comparative Example 23 | (A-10) | 10 | — | 26 | Ta | 38 | 74 | 3.6 | B | C |
| Comparative Example 24 | (A-10) | 10 | — | 26 | Ta | 82 | 74 | 3.6 | C | C |
| Comparative Example 25 | (A-10) | 10 | — | 25 | Cu | 38 | 75 | 3.3 | B | C |
| Comparative Example 26 | (A-10) | 10 | — | 25 | Cu | 82 | 75 | 3.3 | C | C |
| Comparative Example 27 | (A-10) | 10 | — | 25 | Ni | 38 | 75 | 3.3 | B | C |
| Comparative Example 28 | (A-10) | 10 | — | 25 | Ni | 82 | 75 | 3.3 | C | C |
| Comparative Example 29 | (A-10) | 10 | — | 30 | Pt | 38 | 70 | 3.6 | B | C |
| Comparative Example 30 | (A-10) | 10 | — | 30 | Pt | 82 | 70 | 3.6 | C | C |
| Comparative Example 31 | (A-10) | 10 | — | 40 | Fe | 38 | 60 | 2.4 | C | B |
| Comparative Example 32 | (A-10) | 10 | — | 15 | Fe | 82 | 85 | 4.3 | C | B |
| Comparative Example 33 | (A-1) | — | 2 | 30 | M-1 | 26 | 70 | 3.6 | D | C |
| Comparative Example 34 | (A-10) | 10 | — | 30 | M-1 | 26 | 70 | 3.6 | D | C |
| Comparative Example 35 | (A-1) | — | 2 | 25 | M-2 | 31 | 75 | 3.3 | D | D |
| Comparative Example 36 | (A-10) | 10 | — | 25 | M-2 | 31 | 75 | 3.3 | D | D |

[*1]parts by mass based on 100 parts by mass of resin
[*2]amount of binder present in composition The types of resin listed in the tables are shown below:
Resins
(A-1) Butadiene rubber (the trade name BR-150 available from Ube Industries, Ltd.)
(A-2) Isoprene rubber (the trade name IR-2200 available from JSR Corporation)
(A-3) Natural rubber (available from Tigers Polymer Corporation)
(A-4) Styrene-butadiene rubber (the trade name Nipol NSI 16R available from Zeon Corporation)
(A-5) Ethylene-propylene-diene rubber (the trade name JSR EP43 available from JSR Corporation)
(A-6) Acrylonitrile-butadiene rubber (the trade name Nipol DN4050 available from Zeon Corporation)
(A-7) Silicone rubber (the trade name KE-541-U available from Shin-Etsu Chemical Co., Ltd.)
(A-8) Butyl rubber (the trade name BUTYL 268 available from JSR Corporation)
(A-9) Fluorocarbon rubber (the trade name Viton A700 available from DuPont)
(A-10) Bisphenol A epoxy resin (the trade name jER828 available from Mitsubishi Chemical Corporation, epoxy equivalent weight: 190)
(A-11) Bisphenol F epoxy resin (the trade name EPI-CLON 830 available from DIC Corporation, epoxy equivalent weight: 170)
(A-12) Phenol novolac epoxy resin (Product No. 406775 available from Sigma-Aldrich Company, epoxy equivalent weight: 170)
(A-13) Polyimide resin (the trade name PL450C available from Mitsui Chemicals, Inc.)
(A-14) Polyamide resin (the trade name 5013B available from Ube Industries, Ltd.)
(A-15) Polyurethane resin (the trade name C80A available from BASF)
(A-16) Polyvinyl chloride resin (the trade name CB70KA available from Mitsubishi Chemical Corporation)
(A-17) Polyethylene resin (the trade name HI-ZEX MIL-LION 0305 available from Mitsui Chemicals, Inc.)
(A-18) Polyacetal resin (the trade name Iupital F20-03 available from Mitsubishi Engineering-Plastics Corporation)
(A-19) Polycarbonate resin (the trade name Iupilon H-4000 available from Mitsubishi Engineering-Plastics Corporation)
(A-20) Polyetheretherketone resin (the trade name PEEK Polymer 450G available from Victrex plc)
(A-21) Polyamide-imide resin (the trade name Torlon 4203L available from Solvay)
(A-22) Polyphenylene sulfide resin (the trade name FZ-2130 available from DIC Corporation)
(A-23) Fluorocarbon resin (the trade name 807-NX available from DuPont-Mitsui Fluorochemicals Co., Ltd.)
(A-24) Acrylonitrile-butadiene-styrene copolymer (the trade name Denka ABS SE-10 available from Denka Company Limited)

The metal particles used in the comparative examples in the tables are as follows:

(M-1) Tungsten carbide (the trade name NCWC10 available from Nikkoshi Co., Ltd., average particle size: 1.2 μm)

(M-2) Titanium oxide (the trade name KA-10 available from Titan Kogyo, Ltd., average particle size: 0.5 μm)

As shown in Tables 1-1 to 1-3 above, the compositions in which the monodispersity of the metal used was outside the range specified in the present invention (40% to 80%) did not achieve both good formability and uniform acoustic characteristics at the desired high level even though the types of resin and metal particles were varied (Comparative Examples 1 to 36).

In contrast, the compositions in which the monodispersity of the metal used was in the range of 40% to 80% were found to exhibit good formability and more uniform acoustic characteristics in the sheet irrespective of the type of resin or metal particles (Examples 1 to 61).

Although the present invention has been described in conjunction with embodiments thereof, we do not intend to limit our invention in any detail of the description unless otherwise specified. Rather, the invention should be broadly interpreted without departing from the spirit and scope of the invention defined in the attached claims.

This application claims priority to JP2017-212211, filed in Japan on Nov. 1, 2017, the entire contents of which are hereby incorporated herein by reference.

REFERENCE SIGNS LIST 1 acoustic lens
2 acoustic matching layer (acoustic matching sheet)
3 piezoelectric element layer
4 backing material
7 housing
9 cord
10 ultrasound probe

What is claimed is:

1. A resin composition for an acoustic matching layer, comprising:
 a binder including a resin; and
 metal particles having a monodispersity of 40% to 80%, wherein the monodispersity is calculated by equation (1):

monodispersity (%)=(standard deviation of particle sizes of metal particles/average particle size of metal particles)×100.

2. The resin composition for an acoustic matching layer according to claim 1, wherein the metal particles have a monodispersity of 50% to 70%.

3. The resin composition for an acoustic matching layer according to claim 1, wherein the metal particles have a monodispersity of 55% to 65%.

4. The resin composition for an acoustic matching layer according to claim 1, wherein the metal particles include at least one of Zn, Au, Ag, Zr, Ta, W, Fe, Cu, Ni, Pt, or Mo.

5. The resin composition for an acoustic matching layer according to claim 1, wherein the metal particles are present in an amount of 60% to 98% by mass.

6. The resin composition for an acoustic matching layer according to claim 1, wherein the binder includes an epoxy resin and a curing agent.

7. The resin composition for an acoustic matching layer according to claim 1, wherein the binder includes a rubber and an organic peroxide.

8. The resin composition for an acoustic matching layer according to claim 1, wherein the binder includes a thermoplastic resin.

9. An acoustic matching sheet formed from the resin composition for an acoustic matching layer according to claim 1.

10. An acoustic wave probe comprising the acoustic matching sheet according to claim 9 as an acoustic matching layer.

11. An acoustic wave measuring apparatus comprising the acoustic wave probe according to claim 10.

12. The acoustic wave measuring apparatus according to claim 11, wherein the acoustic wave measuring apparatus is an ultrasound diagnostic apparatus.

13. A method for manufacturing an acoustic wave probe, comprising forming an acoustic matching layer on a piezoelectric element using the resin composition for an acoustic matching layer according to claim 1.

14. A material set for an acoustic matching layer, comprising:
 a base resin made of a resin composition including an epoxy resin and metal particles; and
 a curing agent for the epoxy resin,
 the metal particles having a monodispersity of 40% to 80%, wherein the monodispersity is calculated by equation (1):

monodispersity (%)=(standard deviation of particle sizes of metal particles/average particle size of metal particles)×100.

15. A material set for an acoustic matching layer, comprising:
 a base resin made of a resin composition including a rubber and metal particles; and
 a crosslinking agent including an organic peroxide,
 the metal particles having a monodispersity of 40% to 80%, wherein the monodispersity is calculated by equation (1):

monodispersity (%)=(standard deviation of particle sizes of metal particles/average particle size of metal particles)×100.

* * * * *